United States Patent [19]

Ituarte

[11] Patent Number: 4,735,223
[45] Date of Patent: Apr. 5, 1988

[54] PROCESS AND APPARATUS FOR CLEANING AND STERILIZING OF CONTACT LENSES

[76] Inventor: Angel Ituarte, 3 Rue Lyautel, 31600 Muret, France

[21] Appl. No.: 877,833

[22] Filed: Jun. 10, 1986

[30] Foreign Application Priority Data

Jun. 12, 1985 [FR] France ............... 85 08995

[51] Int. Cl.⁴ ............................................. B08B 3/10
[52] U.S. Cl. ................................... 134/58 R; 134/184
[58] Field of Search ............... 134/1, 184, 56 R, 58 R; 68/355; 366/127

[56] References Cited

U.S. PATENT DOCUMENTS

| | | | |
|---|---|---|---|
| 3,151,846 | 10/1964 | George | 134/184 X |
| 3,481,687 | 12/1969 | Fishman | 134/1 X |
| 3,595,532 | 7/1971 | Doyle et al. | 68/355 X |
| 3,640,294 | 2/1972 | Piccolo | 134/1 X |
| 3,871,395 | 3/1975 | Murry | 134/184 X |
| 3,937,236 | 2/1976 | Runnells | 68/355 X |
| 3,973,760 | 8/1976 | Browning et al. | |

FOREIGN PATENT DOCUMENTS

| | | |
|---|---|---|
| 0031152 | 7/1981 | European Pat. Off. |
| 00786145 | 5/1983 | European Pat. Off. |
| 0126665 | 11/1984 | European Pat. Off. |
| 2240742 | 3/1975 | France |
| 1311866 | 11/1982 | France |

*Primary Examiner*—Harvey C. Hornsby
*Assistant Examiner*—Frankie L. Stinson
*Attorney, Agent, or Firm*—Young & Thompson

[57] ABSTRACT

The present invention concerns a process and apparatus for cleaning contact lenses by the association of a thermal treatment with a mechanical vibratory treatment.

The thermal treatment is constituted of:

a first increase in temperature of the liquid containing the said lenses from the ambient temperature (T1) to a temperature (T2) at which the material adhered to the lenses does not undergo denaturation, a series of stoppages and startings of heating permitting the oscillation in temperature between temperature T2 and another temperature T3 less than T2 and greater than T1, finally a second increase in temperature from T3 to another temperature T4 greater than T2.

The vibratory treatment is to be applied in an independent manner with respect to the thermal treatment, either during the entire period between T1 and T2 or during that between T1 and T4.

5 Claims, 2 Drawing Sheets

PROCESS AND APPARATUS FOR CLEANING AND STERILIZING OF CONTACT LENSES

The present invention relates to a process and apparatus for cleaning and sterilizing contact lenses. Cleaning in this sense means removing the foreign material adhered to the lenses.

A portion of this material is constituted by proteins from tears which coagulate under the effect of thermal treatment beginning at a certain threshold temperature. On the other hand a temperature greater than this threshold is necessary to have a more complete sterilization, and thus it is necessary to effect the cleaning at a temperature lower than the said threshold or to effect it prior to the thermal treatment so as to prevent the coagulation of the proteins which are much more difficult to remove once they are denatured.

Finally, the maximum temperature of the thermal treatment must not deteriorate the lenses themselves, and particularly soft lenses. Several apparatus offer thermal treatment cycles, and some propose several alternative cycles (see for example FR No. 2454 811). The thermal treatment cycles are generally constituted by an increase in temperature, a maintenance of this temperature for a predetermined interval and finally by a decrease in temperature, that is to say a cut-off of heating. Several apparatus which associate cleaning by mechanical, generally ultrasonic, vibration with thermal treatment are known. The principle of the thermal treatment cycle is frequently equivalent to that which has just been described.

The present invention proposes another more efficient thermal treatment cycle associated with a means for cleaning by mechanical vibration. The said cycle exposes the lenses to be sterilized to more refined thermal variations than the traditional cycle, so as to increase the efficiency of this said treatment, in a manner independent from the application of the mechanical vibrations.

To this end, and according to an embodiment, the present invention relates to a process for cleaning and sterilizing contact lenses maintained in a liquid medium, by the association of a thermal treatment, essentially for sterilizing them, with a vibratory mechanical treatment essentially for removing the material which is adhered thereto, these two treatments being applied simultaneously for the entire duration of treatment or for a part of this latter, characterized in that the treatment is constituted of:

a first increase in temperature of the said liquid, from the ambient temperature (T1) to a temperature (T2) at which the material adhered to the lenses does not become denatured, a series of stoppages and startings of heating spaced in time such that the temperature of the said liquid oscillates between T2 and another temperature T3 lower than T2 and higher than T1, and finally, a second increase in temperature from T3 to a temperature T4 greater than T2 and at which the complete sterilization is effected, the vibratory mechanical treatment being applied in an independent manner with respect to the thermal application for the entire duration between T1 and T2 or between T1 and T4.

The thermal part of the treatment described above and constituted by a series of repeated heatings alternating with periods of cooling, is known by the name TRYNDAL sterilization.

According to another embodiment, the present invention relates to an apparatus for cleaning and sterilizing contact lenses of the type comprising a piezoelectric transducer for producing mechanical vibrations, this former being placed in contact with the base of a container to be filled with an appropriate liquid and having a housing adapted to receive a case for the contact lenses, an electronic circuit comprising a thermosensitive resistor (R2), a heating unit and an energization circuit characterized by a piezoelectric transducer and a control circuit both energized by a same supply, a heating unit supplied directly by an electrical outlet and regulated, like the piezoelectric transducer, by the said control circuit.

The present invention will be best understood from reading the following detailed description, illustrated by the drawings in which.

Figure 2:
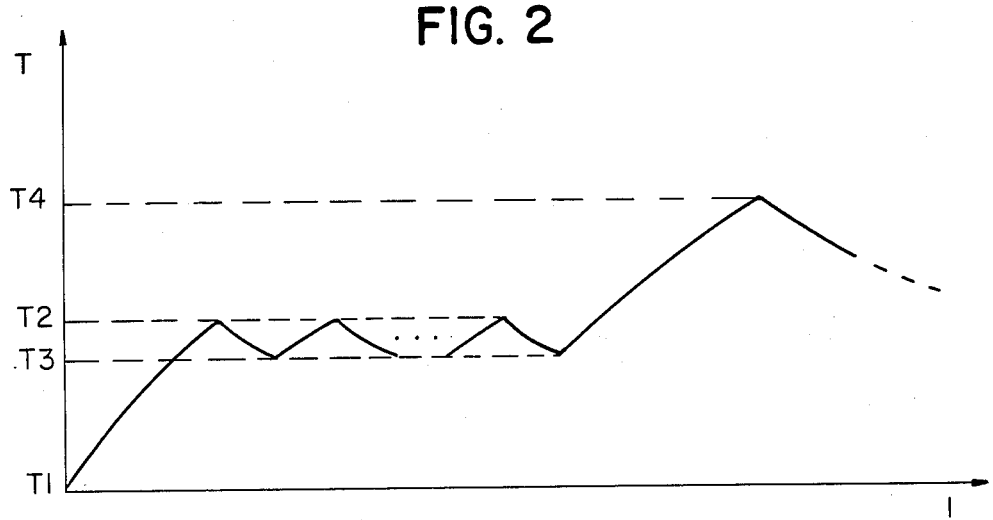
FIG. 2 is a curve which shows the temperature evolution in the container (B) which contains the case for the lenses.
Figure 3:
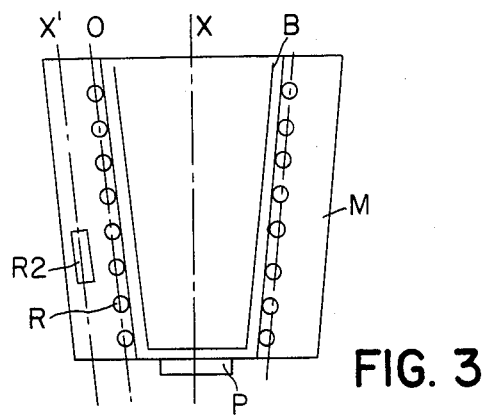
FIG. 3 is a diagram which shows the disposition of the piezoelectric transducer (P), the heating unit R and the thermosensitive resistor R2 with respect to the container (B).

FIGS. (4a) and (4b) show respectively a part of the temperature evolution curve in the container (B), shown in FIG. 2, and the corresponding part of the temperature evolution curve of the disposition of the thermosensitive resistor (R2).

The process according to the invention consists of associating a specific thermal treatment with a mechanical vibratory treatment, so as to sterilize and clean the contact lenses.

The said thermal treatment consists of heating the liquid medium in which the contact lenses are maintained, from the ambient temperature (T1) to a temperature (T2) at which the material adhered to the said lenses is not subject to denaturation, that is to say coagulation (FIG. 2). Our tests have shown that this temperature must be less than 60° C.

The thermal energy furnished to the liquid containing the lenses is not sufficient to initiate coagulation of the proteins adhered to the lenses, issued from the tears of the eyes, but agitates the liquid which contains them as well as the protein molecules themselves. This assists the action of mechanical vibrations which are applied to the said liquid at the same time as this thermal treatment phase.

Once the temperature of the liquid reaches temperature T2, the heating is stopped and the liquid is allowed to cool to a temperature T3 greater than T1, the liquid is heated again to T2 and then the heating is once again stopped. This operation is repeated so that the temperature of the liquid oscillates between T2 and T3 a desired number of times.

The energy to be dissipated in the liquid by application of the mechanical vibrations must not prevent the cooling of the said liquid. This is possible by suitably choosing the power of the piezoelectric transducer.

The liquid is heated to a temperature T4 greater than T2 and at which a complete sterilization is effected.

Causing the temperature to oscillate between T2 and T3 helps make the sterilization efficient in this temperature range, that is to say it helps disrupt the adaptation phenomenon manifested by the microorganisms with respect to thermal change in a single direction.

It will be seen that this causing of the temperature to oscillate may be effected at any temperature level, and at one or several levels.

The mechanical vibratory treatment may be applied to the said liquid either for the entire duration between T1 and T2 or for that between T1 and T4. In this latter case, the cleaning, that is to say the disengaging of the material adhered to the said lenses, will take place for the duration of the thermal treatment: at first for removing the proteins at low temperature and then for disengaging if desired other materials which may be engaged thereto and which do not undergo denaturation under the effect of temperature.

Figure 1:
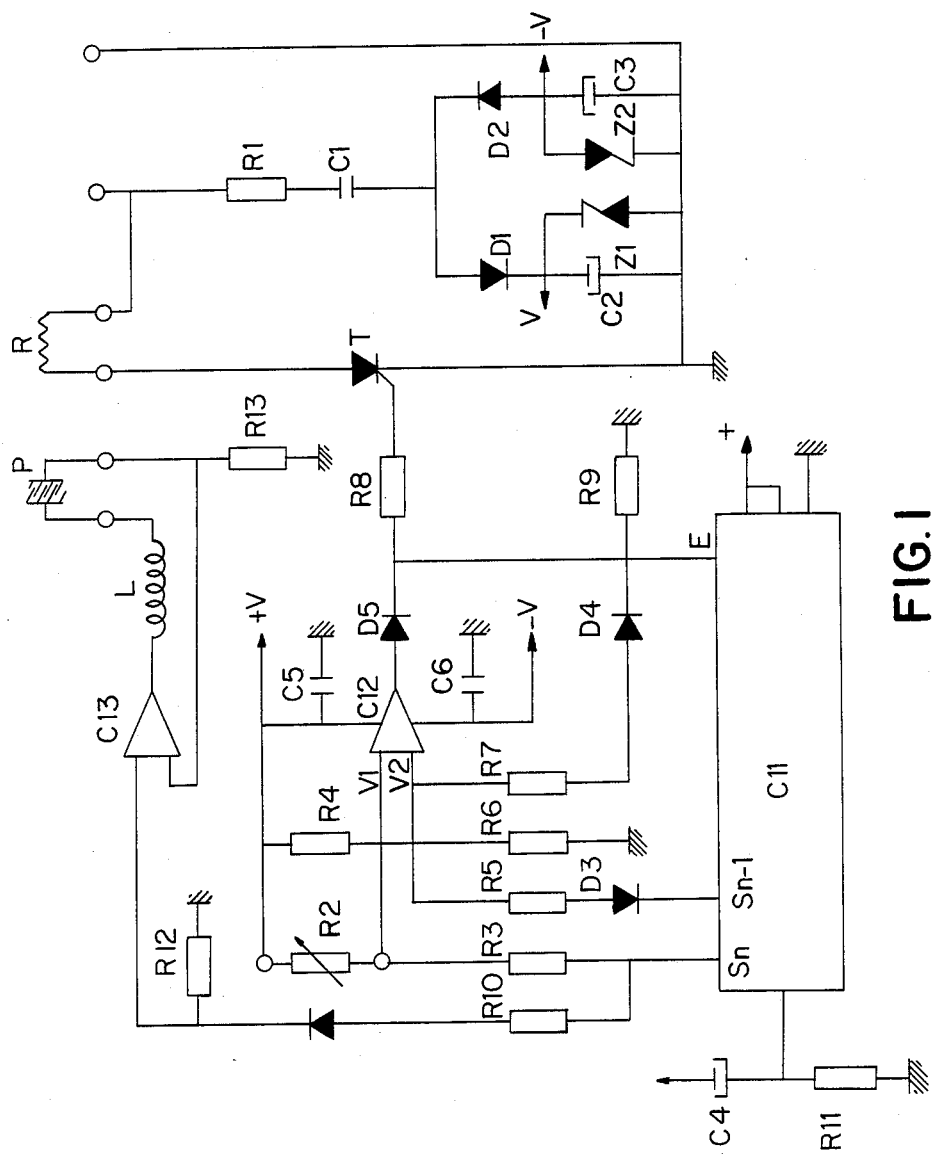
FIG. 1 is an electronic diagram which shows the energization circuit and the various components which control the heating unit R and the piezoelectric transducer P.

The apparatus for practicing the process, and the electronic diagram of which is shown in FIG. 1, is given by way of indicative example.

This apparatus comprises an energization unit which, once connected to the electrical outlet, provides two opposed voltages +V and −V. It is constituted of a resistor R1 and a condenser C1 connected in series, two assemblies each being constituted of a diode, a condenser and a zener diode this latter being intended to limit the voltage. These two assemblies function in opposite directions. The first assembly is constituted by the diode D1, the condenser C2 and the zener diode Z1. The second assembly is constituted by the diode D2, the condenser C3 and the zener diode Z2.

The voltage V is divided by two resistors, a variable thermosensitive resistor R2 and a fixed resistor R3 so as to supply a first voltage V1 on their connection line. The same voltage V is divided between, on the one hand a resistor R4 and on the other hand a series of resistors R5, R6 and R6, so as to provide a second voltage V2 on the connection line of the resistor R4 and the said series.

These two voltages are applied on the two inputs, non-inverting and inverting, respectively notated (+) input and (−) input of a voltage comparator (CI2), for example an operational amplifier, the output of which changes the voltage as a function of the difference between the two voltages applied to the inputs. The voltage on the said output takes either a positive value or the same value but with a negative sign. The said value is substantially equal to V.

The output voltage of CI2 is applied to the trigger of a thyristor (T) so as to render it either conducting or non-conducting, so as to permit the energization of a heating unit (R) supplied directly by the current of the electrical output. If this output voltage is positive, that is to say if V1 is less than V2, the resistor R is heated, departing from the ambient temperature T1 following the authorization of the passage of current through (T). The resistor R7 is blocked because of the positive signal of the output opposed to the signal V2 of the (+) input through the intermediary of a diode (D4) passing in the (+) input-output direction of CI2. The thermosensitive resistor situated in the proximity of (R) is also heated and changes value. In the assembly shown in FIG. 1, (R2) has a negative temperature coefficient, and thus the voltage V1 increases. When V1 becomes greater than V2, that is to say when the temperature T2 is attained, the voltage at the output becomes negative, and consequently the thyristor cuts off the energization of (R) and resistor (R7) becomes conducting, which lowers the value of V2. This permits the cooling of the assembly consitituted by container (B) in which the lenses are maintained in a suitable liquid, the heating unit and the thermosensitive resistor (R2). In order for the heating to begin again, the voltage V1 must be less than the new voltage V2, that is to say the temperature of the assembly must be less than T2. Once voltage V1 becomes less than the new voltage V2, because of cooling, the heating begins again starting from temperature T3 at which V1 equals V2, and continuing to T2.

This energization or de-energization of the heating unit is repeated a desired number of times causing the temperature to oscillate between T2 and T3.

The separation between these two temperatures can be calculated by causing the value of resistor R7 to vary with respect to R5 and R6.

The diode D5 prevents the passage of the negative signal which appears at the output of CI2 when V1 becomes greater than V2.

It is clear that a thermosensitive resistor with a positive temperature coefficient may be used in place of that which is used in the circuit shown, simply by interchanging its position with that of the resistor R3.

A computer (CI1) has an input (E) and n outputs (S): S1, S2 . . . Sn−1, Sn; this computer has a signal the height of which is substantially equal to V at its outputs one after the other in the order from 1 to n. All the outputs, except that which has the said signal, are connected to ground.

The input E of CI1 is connected to the output of CI2. Each time a positive signal appears at the said output, that is to say each time the value of V2 exceeds the value of V1, the computer CI1 is incremented one step. One of these outputs, for example the output Sn−1, is connected to the resistor R5 through the intermediary of a diode D3 conducting in the (+) input of CI2-output Sn−1 direction.

Once the signal of the computer CI1 is presented at output Sn−1, the resistor R5 is no longer traversed by the current and the energization of the heating unit R continues up to a temperature T4 greater than T2. It is clear that this temperature may be calculated by the choice of the resistor R5 relative to R6 and R7. Once this temperature (T4) is attained the heating unit is de-energized and a positive signal appears at the following output of the computer CI1.

The piezoelectric transducer (P) is energized, by the same supply as the control circuit, with alternating current so as to provide mechanical vibrations to be applied to the liquid containing the said contact lenses.

The said piezoelectric transducer (P), having some capacitive effect, is mounted in a resonant circuit (LC) in cooperation with a self-inductance (L). The maintenance of this resonance in time is assured by a voltage comparison means, for example an operational amplifier (CI3) identical to (CI2), the output of which changes the value either positively or negatively according to the difference of the voltages applied to its two inputs (+) and (−).

By energizing CI3, there appears at its output a provisional signal which may be either positive or negative due to its electronic construction. This signal causes, after having traversed (L) and (P), the appearance of a voltage of opposite direction on the (+) input of CI3, which results in completing the charging of (P), like a condenser, up to the maximum level of the output of (CI3).

Upon stoppage of charging of (P), the (+) input of CI3 changes voltage with respect to the ground because of the stoppage of the passage of charge in resistor R13. This half-cycle that has just been described in repeated in an opposite direction following changing of the voltage on the output of CI3. A rectified alternating signal is also applied on the transducer (P).

The advantage of mounting the piezoelectric transducer (P), like a condenser, in a resonance circuit is that the effective voltage applied to it is much less than the supply voltage. The relation between the effective voltage and the supply voltage is on the one hand inversely proportional to the ohmic resistance of the circuit and on the other hand directly proportional to the square root of the inductance divided by the square root of the capacitance.

Upon appearance of a positive signal at the output Sn of (CI1), this signal is found on the (−) input of (CI2) and on the (−) input of (CI3). The voltage at these two inputs will be higher than that applied at the (+) input of each amplifier, which renders the voltage at their output permanently negative and consequently deenergizes the heating and blocks the oscillation of the (LC) circuit.

If the output (Sn) is the last among the outputs of (CI1), the cutting off of the heating and the blockage of the resonant circuit will be maintained up to a new zeroing of CI1.

It is clear that the operation of resistor (R5) may be repeated by the addition of one or several resistors interconnected in parallel and each connected to one of the outputs of CI1 so as to cause to vary in turn the voltage V2 applied at the (+) input of CI2.

The advantage of using a piezoelectric transducer of so great a power as to be able to energize through the same supply as the components of the control circuit, namely (CT1), (CT2) and T4, is that we avoid using either transformers or power components. This renders the apparatus lighter and more compact and we avoid having to provide ventilating systems in the case of using power components.

Figure 4A:
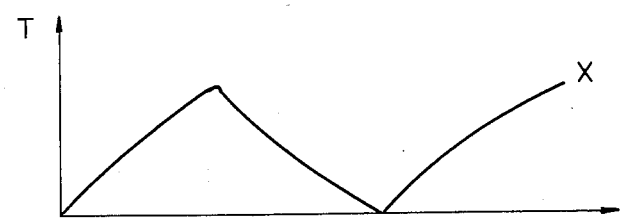
Figure 4B:
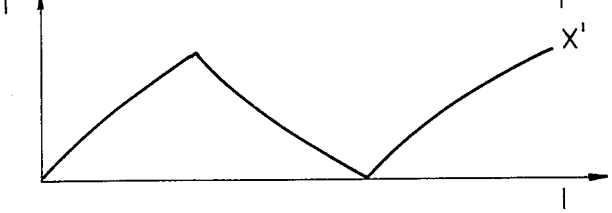

The heating unit (R) is encased in a mass (M) of an appropriate material, conventionally known, in a shape conforming to the container (B), for transferring the heat on the one hand to the said container in which the contact lenses are placed in an appropriate liquid, and on the other hand, to the thermosensitive resistor which is either also encased in the mass (M), or fixed against it exteriorly, or placed remote from it. The positioning of the heating unit (R) and the thermosensitive resistor (R2) are effected in such a manner that the variation in temperature, following the energization or deenergization of the heating unit, on the axis X of the container (B), is identical to that of the surface X' where the resistor (R2) is disposed (FIG. 4a and FIG. 4b).

These positionings are calculated by taking into consideration the capacitance and the thermal conductivity of the material of the container (B), the liquid which fills it, and the mass (M).

The operation of the apparatus is as follows: following the energization:
(a) voltage V1 is lower than V2, thyristor (T) is conducting and consequently the heating unit (R) is energized and the resistor (R7) is blocked.
(b) the piezoelectric transducer is supplied with alternating current and sends mechanical vibrations to the liquid which contains the contact lenses.

When V1 becomes greater than V2, the temperature T2 is attained, thyristor (T) becomes non-conducting and the voltage V2 decreases following deblocking of the resistor R7, permitting the cooling of the assembly.

The heating is carried out again when V1 becomes less than the new value of V2.

This latter step is repeated a desired number of times, causing the temperature to oscillate between T2 and T3.

Following the appearance of a signal at the output Sn−of (CI1), resistor (R5) becomes blocked which causes the voltage V2 to increase and permits the temperature to rise up to the temperature T4, it being noted that the resistor R7 will also be blocked.

Following the appearance of a signal at the output Sn of (CI1), the voltage V1 at the (−) input of (CI3) takes on a higher value, in every case, than those at the (+) inputs of these two comparators, which deenergizes the heating and impedes the oscillation of the (RC) circuit.

It will be noted that the container (B) may be provided with a magnetic agitator, the inductance circuit of which is supplied by the same supply as the piezoelectric transducer (P) and the control circuit. This would disperse the particles detached from the contact lenses into the totality of the liquid.

It goes without saying that the present invention may receive any modifications and variations of the present application.

I claim:

1. In an apparatus for cleaning and sterilizing contact lenses, comprising: a piezoelectric transducer for producing mechanical vibrations and adapted to be disposed adjacent a container for storing contact lenses; and an electric circuit having a thermosensitive resistor (R2), a heating unit, and energization means comprising a first voltage comparison means having first and second inputs and an output controlling energization and deenergization of said heating unit, a first voltage (V1) variable relative to said thermosensitive resistor and a second programmable variable voltage (V2) being applied to said first and second inputs of said first voltage comparison means, respectively, thereby to generate a changing value on said output of said first voltage comparison means alternately to energize and deenergize said heating unit; the improvement in which said circuit comprises means for generating said first and second voltages (V1 and V2) from a constant value voltage (V), comprising a first resistor (R3) series connected to said thermosensitive resistor (R2) with said first input of said first voltage comparison means being connected intermediate said first resistor (R3) and said thermosensitive resistor (R2), and a second resistor (R4) and a series of parallel connected further resistors between which said constant value voltage (V) is divided to generate said second voltage (V2), certain of said further resistors being authorized to conduct or restrict passage of current therethrough.

2. Apparatus according to claim 1, wherein said further resistors comprise a third resistor (R5) connected to an output of a computer (CI1) via a first diode (D3), and a fourth resistor (R7) connected to said output of said first voltage comparison means via a second diode (D4), whereby said first and second diodes are conducting solely when said second voltage (V2) is less than said first voltage (V1).

3. Apparatus according to claim 1, wherein said piezoelectric transducer is supplied with alternating current, comprises an inherent capacitance, and is disposed in a loop of said electric circuit having an inductor and devoid of further capacitative elements, said loop being supplied by a second voltage comparison means, whereby said loop acts as an LC circuit.

4. Apparatus according to claim 3, wherein said electric circuit comprises a computer (CI1) having a plurality of outputs, one of said outputs bearing a signal of amplitude equal to said constant value voltage (V), said computer being incremented one step each time an appropriate signal is supplied to its input, wherein said input of said computer is connected to said output of said first voltage comparison means via a third diode (D5), a second output of said computer being connected to an input of said second voltage comparison means.

5. In an apparatus for cleaning and sterilizing contact lenses, comprising: a piezoelectric transducer for producing mechanical vibrations and adapted to be disposed adjacent a container for storing contact lenses; and an electric circuit having a thermosensitive resistor (R2), a heating unit, and energization means comprising a first voltage comparison means having first and second inputs and an output controlling energization and deenergization of said heating unit, a first voltage (V1) variable relative to said thermosensitive resistor and a second programmable variable voltage (V2) being applied to said first and second inputs of said first voltage comparison means, respectively, thereby to generate a changing value on said output of said first voltage comparison means alternately to energize and deenergize said heating unit; the improvement in which said piezoelectric transducer has an inherent capacitance and is disposed in a loop of said electric circuit supplied by a second voltage comparison means, said loop comprising an inductor and being devoid of further capacitative elements, whereby said inherent capacitance of said transducer and said inductor cause said loop to act as an LC circuit.

* * * * *